(12) United States Patent
Oi et al.

(10) Patent No.: US 8,501,209 B2
(45) Date of Patent: *Aug. 6, 2013

(54) GEL-TYPE WATER ABSORBENT

(75) Inventors: Yukiko Oi, Kanagawa (JP); Keiichi Oyama, Kanagawa (JP); Yuji Uzuhashi, Nagano (JP); Masaaki Kojima, Nagano (JP)

(73) Assignee: The Nisshin Oillio Group, Ltd (JP)

( * ) Notice: Subject to any disclaimer, the term of this patent is extended or adjusted under 35 U.S.C. 154(b) by 1140 days.

This patent is subject to a terminal disclaimer.

(21) Appl. No.: 11/571,022

(22) PCT Filed: May 16, 2005

(86) PCT No.: PCT/JP2005/008857
§ 371 (c)(1),
(2), (4) Date: Dec. 20, 2006

(87) PCT Pub. No.: WO2006/001132
PCT Pub. Date: Jan. 5, 2006

(65) Prior Publication Data
US 2008/0279798 A1    Nov. 13, 2008

(30) Foreign Application Priority Data
Jun. 29, 2004  (JP) ................. 2004-190756

(51) Int. Cl.
*A61K 31/00*  (2006.01)
*A61K 9/00*   (2006.01)
*A01N 45/00*  (2006.01)
*A01N 25/00*  (2006.01)

(52) U.S. Cl.
USPC ............................ 424/418; 424/461; 514/54

(58) Field of Classification Search
USPC ..................... 514/54; 424/418, 461
See application file for complete search history.

(56) References Cited

U.S. PATENT DOCUMENTS

| | | | |
|---|---|---|---|
| 3,399,189 A * | 8/1968 | Gordon | 536/128 |
| 4,074,043 A * | 2/1978 | Jones et al. | 536/52 |
| 4,746,528 A | 5/1988 | Prest et al. | |
| 4,895,938 A | 1/1990 | Teraoka et al. | |
| 5,403,599 A * | 4/1995 | Whistler | 426/48 |
| 6,056,950 A * | 5/2000 | Saettone et al. | 424/78.04 |
| 2003/0113356 A1* | 6/2003 | Deckner et al. | 424/401 |
| 2004/0014717 A1 | 1/2004 | Adachi et al. | |
| 2005/0118210 A1* | 6/2005 | Kachi et al. | 424/401 |

FOREIGN PATENT DOCUMENTS

| | | |
|---|---|---|
| EP | 1 323 773 A1 | 7/2003 |
| EP | 1323773 | 7/2003 |
| JP | 52-111597 | 9/1977 |
| JP | 56-139572 | 10/1981 |
| JP | 61-185541 | 8/1986 |
| JP | 64-022901 | 1/1989 |
| JP | 64-040542 | 2/1989 |
| JP | 64-074239 | 3/1989 |
| JP | 04-210639 | 7/1992 |
| JP | 10-248505 | 9/1998 |
| JP | 2000-354460 | 12/2000 |
| JP | 2002-060546 | 2/2002 |
| JP | 2003-82003 | 3/2003 |

OTHER PUBLICATIONS

Antimicrobial Agents and Chemotherapy, Sep. 2004, vol. 48, No. 9, pp. 3396-3401.*
Multivalent. (2012). In thefreedictionary.com. Retrieved Sep. 24, 2012, from: http://www.websters-online-dictionary.org/definitions/Multivalent.*
Supplemental European Search Report dated Jun. 8, 2009 which issued in connection with corresponding European Application No. 05739297.9.
NTS Inc.; Gel Handbook; Nov. 28, 1997; Japan.

* cited by examiner

*Primary Examiner* — Fereydoun G Sajjadi
*Assistant Examiner* — Courtney Brown
(74) *Attorney, Agent, or Firm* — Clark Hill PLC

(57) ABSTRACT

The invention provides a gel-type water absorbent with rich flexibility and elasticity, with less variation in strength of gel during preservation, with low viscosity of sol, with easy processability, having a physical property with extremely less water discharge, and having functions of water absorbency and water solubility. The gel-type water absorbent contains a tamarind seed polysaccharide including 90% or more dietary fiber, 1% or less protein and 1% or less ash; and a water-soluble organic substance including at least one or more of a polyhydric alcohol and water-soluble surfactant.

6 Claims, No Drawings

GEL-TYPE WATER ABSORBENT

RELATED APPLICATION (PRIORITY CLAIM)

This application is a National Phase filing regarding International Application No. PCT/JP2005/008857 filed on May 16, 2005, which claims priority from Japanese Patent Application No. 2004-190756 filed on Jun. 29, 2004.

TECHNICAL FIELD

The present invention relates to a gel-type water absorbent with rich flexibility and elasticity, with excellent processability, with less variation in strength, and having water absorbency.

BACKGROUND ART

Aqueous gel materials have been widely used in medicines, medical instruments, medicinal materials, cosmetics, living sundries, architectural materials, paints, chemicals, photos and so forth. They include such raw material as an aqueous synthetic polymer and a natural polymer. Typical aqueous synthetic polymers include polyvinyl alcohol, and cross-linked sodium polyacrylate.

On the other hand, typical natural polymers include agar, carrageenan, gelatin, and gellan gum, which have been subjected to trial applications in foods as natural polysaccharides to form aqueous compositions having viscosity or viscoelasticity. Such the polysaccharides have also been blended in fragrances, and deodorants, and also utilized as gelling agents (see Patent Document 1, Patent Document 2, Patent Document 3 and Patent Document 4).

These days, in relation to problems of wastes loaded on environments, materials with merits, such as material biodegradable after disposal and material processable by recycling, have been developed. In general, polymeric agent materials such as polymers of lactic acid and amino acid have been developed as the biodegradable material, and utilization of polyethylene terephthalate (PET) has proceeded in terms of recycling.

Available water-containing materials include various gelling agents, typically polyvinyl alcohol, and cross-linked sodium polyacrylate. Among those, natural materials are particularly advantageous and significant in environmental issues because of biodegradation on disposal and safety to human. They are materials having wide versatility and available with safety in any industrial fields without consideration of loads on environments, such as disposed water, disposed gases and disposed solvents resulted from chemical synthesis.

Patent Document 1: JP 61-185541 A
Patent Document 2: JP 1-40542 A
Patent Document 3: JP 1-74239 A
Patent Document 4: JP 10-248505 A

DISCLOSURE OF THE INVENTION

Problem to be Solved by the Invention

Natural polysaccharides have been subjected to several trial applications mainly in foods as described above. As for carrageenan and gellan gum conventionally used as a base material, an increase in the amount of mixture to enhance the rupture strength results in an aqueous composition with extreme water discharge and poor flexibility as a problem. In addition, as they are required to react with ions of a metal such as calcium and magnesium, the reaction is irreversible and they can not be reused as a problem. The gel of agar also has a large water discharge, and exhibits solid physical property with high rupture strength though it is poor in flexibility, hard, and fragile. Gelatin yields soft gel but the strength is low and the gel melts at 40° C. or higher as a problem.

Aqueous gel materials originated from these natural gelling agents discharge moisture over time due to evaporative dissipation but have no water absorbency. Accordingly, they can not be employed in the use for the purpose of water absorbency. Still more, they can not be reused by absorbing water after they discharge moisture.

The water absorbency mentioned in the present invention means the presence of a function of absorbing water on contact with water and differs from the so-called humidity absorbency when left in the atmosphere. With the merit of the water absorbency, an aqueous gel can be reused after it dissipates moisture in the atmosphere and then absorbs water for restoration when it is given moisture. It is greatly aimed at reducing resource consumption and decreasing wastes.

On the other hand, the mixed use of galactomannans and xanthan gum has been known to form strong gel with almost no water discharge and disclosed in, for example, JP 2002-060546 A. They have excellent properties such as flexibility and water absorbency as aqueous gel while the high viscosity of sol extremely worsens handling on production even when it is heated and requires mechanical operations such as pressurizing and depressurizing on production lines of processing and filling. Thus, there is a limit for the use thereof. Usually, processing requires heating up to 80-90° C. Therefore, a highly volatile substance and a thermally unstable component can not be mixed with them as a problem. Such the materials have water absorbency but the speed is slow and accordingly reprocessing is troublesome. These water-soluble polymeric materials exhibit no water solubility at normal temperature and accordingly can not be drained for disposal. Therefore, disposals of these materials require disposals as wet garbage and burnable garbage, causing a problem.

The present invention has an object to provide a gel-type water absorbent with rich flexibility and elasticity, with less variation in strength of gel during preservation, with low viscosity of sol, with easy processability, having a physical property with extremely less water discharge, and having functions of water absorbency and water solubility.

Means to Solve the Problem

The inventors et al. have intensively studied to solve the above problems and resultantly found that a gel-type water absorbent containing a certain specific tamarind seed polysaccharide and a water-soluble organic substance is rich in flexibility and elasticity, with less variation in strength of gel during preservation, with low viscosity of sol, with easy processability, with extremely less water discharge, and having all functions of water absorbency and water solubility. The present invention has been made based on the above knowledge and is directed to a gel-type water absorbent, which contains a tamarind seed polysaccharide including 90% or more dietary fiber, 1% or less protein and 1% or less ash; and a water-soluble organic substance including at least one or more of a polyhydric alcohol and a water-soluble surfactant.

In the gel-type water absorbent according to the present invention, the tamarind seed polysaccharide includes 92% or more dietary fiber, 0.5% or less protein and 0.5% or less ash, preferably. More preferably, the gel-type water absorbent contains 2-50% the tamarind seed polysaccharide and 3-50% the water-soluble organic substance. Preferably, the gel-type water absorbent further contains a volatile active ingredient. Preferably, in the gel-type water absorbent according to the present invention, the water-soluble organic substance includes at least one or more of a polyhydric alcohol with 2-5 valences and a water-soluble surfactant with an HLB value of 10-20.

The present invention also provides a fragrance, a deodorant, a dehumidifying agent, a patch, and a fishing lure, which comprise as a base material the gel-type water absorbent of the present invention.

The tamarind seed polysaccharide is a polysaccharide extracted from seeds of *tamarindus indica*, a perennial pulse plant living all over Southeast Asia including India and Myanmar. In general, they can be dissolved completely in water when heated up to 80° C. or higher. An aqueous solution thereof is almost given Newton viscosity, excellent in acid-proof, heat-resisting property and salt resistance, and widely employed in the food field generally. They have been known to form aqueous gel in the presence of saccharide such as sugar and millet jelly, or of ethanol. General tamarind seed polysaccharides, however, have elasticity with low flexibility, much moisture discharged from aqueous gel, having weak water absorbent, with remarkable variation in rupture strength of gel during preservation. Accordingly, they have been not utilized much as materials in various industrial fields. As an example of industrial application, they have been used for jellified foods having water discharge-preferred textures. In cosmetics industry, they have been used not as gelling agents but only as humidifying agents.

Effect of the Invention

As above, the present invention can provide a gel-type water absorbent with rich flexibility and elasticity, with less variation in strength during preservation, with low viscosity of sol, with easy processability, with extremely less water discharge, and having functions of water absorbency and water solubility. The gel-type water absorbent according to the present invention is thus rich in water absorbency. Accordingly, even when it is used as a gelling agent and discharges moisture, it can be reused after subjected to water absorption. In addition, the gel-type water absorbent according to the present invention has water solubility. Accordingly, when it is abandoned, it can be dissolved in water and disposed as abandoned water.

With such the characteristics, the gel-type water absorbent according to the present invention can be widely utilized in industrial fields of medicines, medical instruments, medicinal materials, house-wares, and sundries for home use, and of architectural materials, agrichemicals, feed stuff, fertilizers, paints, ink, ceramics, resins and adhesives as well. It can be utilized in various forms such as spherical, square, rod-like, and film-like because it can be molded freely.

THE BEST MODE FOR CARRYING OUT THE INVENTION

The gel-type water absorbent according to the present invention will now be described below in detail. The gel-type water absorbent according to the present invention basically comprises a tamarind seed polysaccharide and a water-soluble organic substance.

The first description is given to the tamarind seed polysaccharide, a component of the gel-type water absorbent of the present invention. The tamarind seed polysaccharide used in the present invention is a tamarind seed polysaccharide that includes 90% or more dietary fiber, 1% or less protein and 1% or less ash, which is highly purified by removing or reducing water-insoluble components compared to general-purposed tamarind seed polysaccharides. Preferably, a tamarind seed polysaccharide including 92% or more dietary fiber, 0.5% or less protein and 0.5% or less ash may be employed. The amount of the tamarind seed polysaccharide mixed is preferably 2-50%, more preferably 4-40%, and yet more preferably 5-20%, of the gel-type water absorbent.

An example of the method of analyzing dietary fiber contained in the tamarind seed polysaccharide includes an enzyme-weight method (Prosky-AOAC method). An example of the method of analyzing protein includes a semimicro-Kjeldahl method, that is, a nitrogen determination described in the official compilation of food additives. The weight of nitrogen (N) in 0.5 g of the sample may be measured and then multiplied by 5.7 for determination (0.01 N sulfuric acid 1 ml=0.1401 mg N). An example of the method of analyzing ash includes the following one that is described in the official compilation of food additives. In this example, 1 g of a sample is collected, then gently heated for carbonization, and intensively heated up to 500-600° C. until no carbide is found and the weight becomes constant, followed by measurement of the amount of the residue.

In the present invention, a gel-type water absorbent with rich flexibility and elasticity, with less variation in strength of gel during preservation, with low viscosity of sol, with easy processability, with extremely less water discharge, and having a function of water absorbency may be acquired with the use of a tamarind seed polysaccharide from which part or all of water-insoluble components have been decomposed and/or removed. The decomposition of the water-insoluble component generally includes hydrolysis with an alkali or acid and hydrolysis with an enzyme while the removal thereof includes treatment with an adsorbent such as diatom, terra alba, active carbon, other clays, and ceramics, as disclosed in JP 2003-82003 A. A tamarind gum purified in this way is commercially available. For example, the NOM Coat EP-2 available from Nisshin OilliO Ltd. can be employed to acquire a gel-type water absorbent, which is given a physical property with rich flexibility and elasticity, with less variation in strength during preservation, with less water discharge, and functions of high water absorbency and water solubility. The use of general tamarind seed gums not subjected to the above treatment and less purified can not satisfy functions in terms of flexibility, gel stability, water discharge, water absorbency, and water solubility.

The following description is given to the water-soluble organic substance, a component of the gel-type water absorbent according to the present invention. The water-soluble organic substance used in the present invention includes at least one or more of a polyhydric alcohol and a water-soluble surfactant, which may be not limited in particular so long as they are commercially marketed and distributed. Examples of the polyhydric alcohol include ethylene glycol, diethylene glycol, polyethylene glycol, propylene glycol, dipropylene glycol, tripropylene glycol, polyethylene glycol, trimethylene glycol, 1,2-butylene glycol, 1,3-butylene glycol, hexylene glycol, 1,2-pentane diol, 1,2-hexane diol, erythritol, glycerin, diglycerin, triglycerin, polyglycerin, pentaerythritol, dipentaerythritol, and xylitol. Among those, polyhydric alcohols with 2-5 valences are preferable. In addition, as other substances, especially preferable examples of the water-soluble surfactant with an HLB value of 10-20 may include polyglycerin fatty acid ester, polyethylene glycol fatty acid ester, polyoxyethylene alkyl ester, polyoxyethylene sorbitan fatty acid ester, saccharose fatty acid ester, and alkyl glucoside. These are most preferably used together with the above polyhydric alcohol. If the above water-soluble organic substance is not contained, an aqueous solution is produced instead of gel.

To yield a gel-type water absorbent rich in elasticity with flexibility, with less variation in strength during preservation, with extremely less water discharge, and having a function of water absorbency, a total amount of the water-soluble organic substance mixed is preferably 3-50% by weight, more preferably 10-40% by weight, and further more preferably 20-35% by weight, of the gel-type water absorbent.

The gel-type water absorbent according to the present invention forms a three-dimensional cross-linked structure including a polymeric compound swollen in an aqueous solution or the liquid phase of an o/w-type emulsion. It has elasticity without fluidity like gel of agar or gelatin and exhibits a solid-like property. The gel-type water absorbent according to the present invention has low viscosity in the state of sol on heating. Accordingly, on mixture of a thermally unstable substance or a highly volatile substance, the mixture can be achieved without imposing an excessive heat history. In addition, the transition from gel to sol arises at a temperature of 50° C. or below, which is a preservation temperature or within a temperature range that hardly varies the condition during transportation. Therefore, it has wide versatility and can exert the effect on fragrances, deodorants, patches, lures, and dehumidifying agents.

The gel-type water absorbent of the present invention may further contain a volatile active ingredient, preferably, in addition to the tamarind seed polysaccharide and the water-soluble organic substance. The volatile active ingredient is a component (substance and/or mixture) that volatilizes to exert an action/effectiveness on human and other living things. For example, it may include a repellent, an insecticide, a germicide, a deodorant, and a fragrance.

The gel-type water absorbent of the present invention may be mixed with other components such as water-soluble polymers, surfactants, oil agents in solid, semisolid and liquid states, inorganic salts, organic salts, preservatives/antibacterial agents, antioxidants, and fragrances, in accordance with the purpose of the physical property. The mixture of other components causes no problem so long as it does not harm the property of the present invention.

Several examples of the water-soluble polymer, though they are not particularly limited, may include plant polymers such as locust bean gum, gum arabic, guar gum, carrageenan, pectin, and quince; microorganism polymers such as xanthan gum, dextran, succinoglucan, pullulan, and curdlan; animal polymers such as collagen, casein, and gelatin; cellulose polymers such as methyl cellulose, ethyl cellulose, hydroxypropyl methyl cellulose, and carboxymethyl cellulose; vinyl polymers such as polyvinyl methyl ether, and carboxyvinyl polymer; and acrylic polymers such as polyacrylate, polymethacrylate, polyethyl acrylate, and polyacryl amide.

Examples of the surfactant may include nonionic surfactants such as polyglycerin fatty acid ester, polyethylene glycol fatty acid ester, polyoxyethylene alkyl ether, polyoxyethylene fatty acid ester, polyoxyethylene sorbitan fatty acid ester, polyoxyethylene sorbitol fatty acid ester, polyoxyethylene glycerin fatty acid ester, polyoxyethylene propylene glycol fatty acid ester, polyoxyethylene castor oil, and polyoxyethylene hardened castor oil; and anionic surfactants such as fatty acid soap (e.g. sodium stearate and triethanolamine palmitate), alkylbenzen sulfonate, alkylether carbonic acid and salts thereof, condensed carbonates of amino acid and fatty acid, alkyl sulfonate, dialkyl sulfosuccinate, sulfonate of fatty acid ester, sulfonate of fatty acid amide, polyoxyethylene alkyl sulfate, alkyl phosphate, and N-acylamino acid-based activator.

Examples of the oil agent may include natural animal/plant oils and fats, and semi-synthesized oils and fats, hydrocarbon oils, higher fatty acids, ester oils, and silicone oils. Examples of the natural animal/plant oils and fats and semi-synthesized oils and fats may include avocado oil, linseed oil, almond oil, olive oil, carnauba wax, candelilla wax, beef tallow, cow leg fat, cow bone fat, hardened beef tallow, wheat germ oil, sesame oil, rice germ oil, rice bran oil, safflower oil, soy bean oil, camellia oil, evening primrose oil, corn oil, rape seed oil, horse tallow, palm oil, palm core oil, castor oil, hardened castor oil, sunflower oil, jojoba oil, macadamia nut oil, beeswax oil, mink oil, cottonseed oil, coconut oil, hardened coconut oil, peanut oil, lanolin, liquid lanolin, reducedlanolin, lanolinalcohol, lanolinfattyacidisopropyl, POE lanolin alcohol ether, lanolin fatty acid polyethylene glycol, and POE hydrogen-added lanolin alcohol ester. Examples of the hydrocarbon may include squalane, squalene, ceresin, paraffin, paraffin wax, fluidized paraffin, microcrystalline wax, and vaseline. Examples of the higher fatty acid may include lauric acid, myristic acid, palmitic acid, stearic acid, behenic acid, undecylenic acid, oleic acid, linoleic acid, linolenic acid, isostearic acid, and 12-hydroxystearic acid. Examples of the ester oil may include diisobutyl adipate, 2-hexyldecyl adipate, di-2-heptylundecyl adipate, isostearyl isostearate, trimethylol propane triisostearate, cetyl 2-ethylhexanate, neopentyl glycol di-2-ethylhexanate, trimethylol propane tri-2-ethylhexanate, pentaerythritol tetra-2-ethylhexanate, cetyl octanate, oleyl oleate, octyldodecyl oleate, decyl oleate, neopentyl glycol dicaprylate, 2-ethylhexyl succinate, isocetyl stearate, butyl stearate, diisopropyl sebacate, cetyl lactate, myristyl lactate, 2-ethylhexyl palmitate, 2-hexyldecyl palmitate, 2-heptylundecyl palmitate, cholesteryl 12-hydroxy stearate, and diisostearyl malate. Examples of the glyceride oil may include glyceride triisooctate, glyceride triisostearate, glyceride triisopalmitate, glyceride tri-2-ethylhexanate, and glyceride trimyristylate. Examples of the silicone oil may include higher alkoxy modified silicone such as dimethyl polysiloxane, methylphenyl polysiloxane, methylhydrogen polysiloxane, octamethyl cyclopenta siloxane, dodecamethyl cyclohexa siloxane, and stearoxy silicone; alkyl modified silicone; higher fatty acid ester modified silicone; and higher fatty acid ether modified silicone.

Examples of the inorganic salt specifically include sodium chloride, potassium chloride, calcium chloride, magnesium chloride, sodium sulfate, magnesium sulfate, sodium carbonate, sodium hydrogencarbonate, and sodium phosphate, which can be used solely or in combination of two or more.

Examples of the organic salt may include sodium citrate, sodium malate, sodium gluconate, sodium lactate, sodium succinate, and sodium tartate, which can be used solely or in combination of two or more.

Examples of the preservative/antibacterial agent may include paraoxybenzonate alkylester, benzonic acid, sodium benzonate, sorbic acid, potassium sorbicate, phenoxyethanols, salicylic acid, and benzalkonium chloride.

Examples of the antioxidant may include tocopherol, butylhydroxy anisole, and dibutylhydroxy toluene.

Examples of the fragrance specifically include α-amylcinnam aldehyde, methyl anthranilate, isoeugnol, γ-undecalacton, ethylvanillin, eugnol, coumarin, cinnamalcohol, cinnamaldehyde, methyl cinnamate, ethyl cinnamate, geraniol, geranyl acetate, citronellyl acetate, cinnamyl acetate, terpinyl acetate, phenylethyl acetate, butyl acetate, isoamyl acetate, 1-menthyl acetate, linalyl acetate, methyl salicylate, citronellol, citronellal, decylaldehyde, γ-nonalacton, vanillin, paramethyl acetophenon, hydroxypropyl cellulose, piperonal, phenylethyl alcohol, ethyl phenylacetate, benzyl alcohol, methylphenylpolysiloxane, 1-menthol, ionone, linanol, citral, borneol, terpinelol, nerolin, diphenyl oxide, acinic aldehyde, dl-camphor, turpentine oil, eucalyptus oil, nutmeg oil, cedar leaf oil, musk oil, ambergris, lavender oil, thymol., and mixtures thereof. These fragrances include not only those that simply release a fragrant odor, but also those that have an effect to spiritually relax a person, such as lavender oil, those that have an effect to awake a person who sniffs the odor, such as eucalyptus oil and citronellal, and those that have an effect to refresh a person, such as 1-menthol.

A method of producing the gel-type water absorbent of the present invention, though it is not limited particularly, comprises: dispersing a tamarind seed polysaccharide in water that contains a water-soluble organic substance, using a propeller or the like; then heating it up to 65° C. or higher but below 95° C. for dissolution; thereafter adding a desired mixing component at a temperature (normally 40-90° C.) in accordance with the property of the component; and pouring it into a preferable mold and cooling it down to 10-30° C. to obtain a gel-type water absorbent. According to circumstances, the gel-type water absorbent may be obtained by evaporating moisture in a drier or the like to adjust the quantity of moisture. Heat-sensitive substances such as fragrances, thermally unstable substances and volatile substances should be added at extremely low temperatures.

The gel-type water absorbent according to the present invention may be applied in base materials for fragrances, deodorants, drying agents, and patches; water absorbing resins for sanitary goods for use in female, infant and senior cares; biodegradation-required toys; and pseudo-materials having biological elasticity.

EXAMPLES

The present invention will be specifically described below with reference to Examples, which are used to demonstrate the present invention and not intended to limit the present invention. The amount of mixture in the following Examples and Comparative examples is expressed as a mass percent (%).

(1) Preparation of Tamarind Seed Polysaccharide

First, a tamarind seed polysaccharide commercially available (from Dainihon Pharmacy: Sample No. 4 in Table 1) was processed as follows to obtain tamarind seed polysaccharides shown in Table 1. A powder of 100 g of the tamarind seed polysaccharide is dispersed in 10 liters of water and heated for dissolution. This solution was treated with active carbon and then precisely filtered. An alcohol was added to this solution until precipitation occurs. The resultant precipitate was then dried and pulverized to obtain a sample. The amount of the added active carbon was varied to obtain samples Nos. 1-3 and 5. Nos. 1-3 tamarind seed polysaccharides were used in Examples of the present invention while Nos. 4 and 5 tamarind seed polysaccharides were used in Comparative examples.

TABLE 1

|  | No. | Dietary Fiber (%) | Protein (%) | Ash (%) |
| --- | --- | --- | --- | --- |
| Tamarind seed gums for the invention | 1 | 93.0 | 0.3 | 0.2 |
|  | 2 | 92.7 | 0.3 | 0.6 |
|  | 3 | 92.1 | 0.6 | 0.9 |
| Tamarind seed gums for Comparative example | 4 | 87.4 | 2.0 | 3.9 |
|  | 5 | 90.4 | 1.1 | 2.1 |

(2) Preparation of Gel-type Water Absorbent

In accordance with mixture compositions in Tables 2-4, all components were mixed and agitated at 25° C. while heating was started, and then they were agitated for dissolution at 80° C. for 30 minutes. Solutions of sol for use in gel-type water absorbents of Examples 1-9 and Comparative examples 1-6 were obtained each with a total amount of 500 g.

TABLE 2

| No. Component | Example 1 (%) | 2 (%) | 3 (%) | 4 (%) | 5 (%) |
| --- | --- | --- | --- | --- | --- |
| Tamarind seed gum No. 1 | 3 | 4 | 5 | — | — |
| Tamarind seed gum No. 2 | — | — | — | 3 | — |
| Tamarind seed gum No. 3 | — | — | — | — | 5 |
| Tamarind seed gum No. 4 | — | — | — | — | — |
| Tamarind seed gum No. 5 | — | — | — | — | — |
| Locust bean gum[1] | — | — | — | — | — |
| Xanthan gum[2] | — | — | — | — | — |
| Agar[3] | — | — | — | — | — |
| Gelatin[4] | — | — | — | — | — |
| Glycerin | 30 | — | — | — | — |
| 1,3-butylene glycol | — | 20 | — | — | — |
| Propylene glycol | — | — | 20 | — | — |
| Ethanol | — | — | — | 10 | — |
| Sorbitol | — | — | — | — | 28 |
| Polysorbate-20[5] | — | — | — | — | — |
| Sodium alkylbenzen sulfonate[6] | — | — | — | — | — |
| Monooleic acid polyglyceryl-10[7] | — | — | — | — | — |
| Purified water | Rest | ← | ← | ← | ← |
| Total | 100 | ← | ← | ← | ← |

[1]Sample (INAGEL L-85 from Ina Foods)
[2]Commodity (ECHOGUM from CP Kelco)
[3]Sample (INAAGAR S-7 from Ina Foods)
[4]Commodity
[5]Commodity (RHEODOL SUPER TW-L120, HLB 16.7, from Kao)
[6]Commodity (NEOPELEX F-65 from Kao)
[7]Commodity (SUNSOFT Q-17S from Taiyo Chemistries)

TABLE 3

| No. Component | Example 6 (%) | 7 (%) | 8 (%) | 9 (%) |
| --- | --- | --- | --- | --- |
| Tamarind seed gum No. 1 | 5 | 5 | 5 | 5 |
| Tamarind seed gum No. 2 | — | — | — | — |
| Tamarind seed gum No. 3 | — | — | — | — |
| Tamarind seed gum No. 4 | — | — | — | — |
| Tamarind seed gum No. 5 | — | — | — | — |
| Locust bean gum | — | — | — | — |
| Xanthan gum | — | — | — | — |
| Agar | — | — | — | — |
| Gelatin | — | — | — | — |
| Glycerin | — | — | — | — |
| 1,3-butylene glycol | 20 | — | 20 | 20 |
| Propylene glycol | — | — | — | — |
| Ethanol | — | — | — | — |
| Sorbitol | — | — | — | — |
| Polysorbate-20 | 3.5 | 3.5 | — | — |

TABLE 3-continued

| No. Component | Example 6 (%) | 7 (%) | 8 (%) | 9 (%) |
|---|---|---|---|---|
| Sodium alkylbenzen sulfonate | — | — | 5 | — |
| Monooleic acid polyglyceryl-10 | — | — | — | 5 |
| Purified water | Rest | ← | ← | ← |
| Total | 100 | ← | ← | ← |

TABLE 4

| No. Component | Comparative example 1 (%) | 2 (%) | 3 (%) | 4 (%) | 5 (%) | 6 (%) |
|---|---|---|---|---|---|---|
| Tamarind seed gum No. 1 | 4 | — | — | — | — | — |
| Tamarind seed gum No. 2 | — | — | — | — | — | — |
| Tamarind seed gum No. 3 | — | — | — | — | — | — |
| Tamarind seed gum No. 4 | — | 4 | — | — | — | — |
| Tamarind seed gum No. 5 | — | — | 4 | — | — | — |
| Locust bean gum | — | — | — | 1.5 | — | — |
| Xanthan gum | — | — | — | 1.5 | — | — |
| Agar | — | — | — | — | 1 | — |

TABLE 4-continued

| No. Component | Comparative example 1 (%) | 2 (%) | 3 (%) | 4 (%) | 5 (%) | 6 (%) |
|---|---|---|---|---|---|---|
| Propylene glycol | — | — | — | — | — | — |
| Ethanol | — | — | — | — | — | — |
| Sorbitol | — | — | — | — | — | — |
| Polysorbate-20 | — | — | — | — | — | — |
| Sodium alkylbenzen sulfonate | — | — | — | — | — | — |
| Monooleic acid polyglyceryl-10 | — | — | — | — | — | — |
| Purified water | Rest | ← | ← | ← | ← | ← |
| Total | 100 | ← | ← | ← | ← | ← |

(3) Viscosity Measurement of Sol and Evaluation

The solutions of the gel-type water absorbents (Examples 1-9 and Comparative examples 1-6) adjusted in (2) were subjected to measurements of viscosity, and readings after one minute from a BL-type viscometer (from Toki Industries), 12 rpm, at 60° C. were converted into viscosity values. The viscosity of the solution below 10000 mPa·s makes the work easy (easy handling) while that above 30000 mPa·s makes it difficult. Therefore, evaluations are indicated with the marks ○ (below 10000 mPa·s), Δ (10000-below 30000 mPa·s), and x (30000 mPa·s or more). These measured results and evaluations are shown in Tables 5 and 6.

TABLE 5

| No. | Example 1 | 2 | 3 | 4 | 5 | 6 | 7 | 8 | 9 |
|---|---|---|---|---|---|---|---|---|---|
| Sol | | | | | | | | | |
| Viscosity | 3300 | 5600 | 8240 | 4250 | 8060 | 8800 | 9040 | 8600 | 9800 |
| Decision | ○ | ○ | ○ | ○ | ○ | ○ | ○ | ○ | ○ |
| Rupture test | ○ | ○ | ○ | ○ | ○ | ○ | ○ | ○ | ○ |
| Preservation test | | | | | | | | | |
| Before Preservation | 576 | 1695 | 1882 | 876 | 1773 | 1777 | 698 | 1858 | 1678 |
| After Preservation | 720 | 2000 | 1998 | 1207 | 1985 | 1910 | 854 | 1988 | 1967 |
| Decision | ○ | ○ | ○ | ○ | ○ | ○ | ○ | ○ | ○ |
| Water discharge phenomenon | | | | | | | | | |
| Amount of moisture | 0 | 0.2 | 0.5 | 0 | 0 | 0 | 0.5 | 0 | 0 |
| Decision | ○ | ○ | ○ | ○ | ○ | ○ | ○ | ○ | ○ |
| Water absorbency | | | | | | | | | |
| Amount of moisture | 95 | 85 | 83 | 90 | 80 | 98 | 90 | 98 | 98 |
| Decision | ○ | ○ | ○ | ○ | ○ | ○ | ○ | ○ | ○ |
| Dried product water absorbency | | | | | | | | | |
| Decision | ○ | ○ | ○ | ○ | ○ | ○ | ○ | ○ | ○ |
| Gel dissolubility | | | | | | | | | |
| Decision | ○ | ○ | ○ | ○ | ○ | ○ | ○ | ○ | ○ |
| Remarks | | | | | | | | | |

TABLE 4-continued

| No. Component | Comparative example 1 (%) | 2 (%) | 3 (%) | 4 (%) | 5 (%) | 6 (%) |
|---|---|---|---|---|---|---|
| Gelatin | — | — | — | — | — | 2 |
| Glycerin | — | — | — | — | — | — |
| 1,3-butylene glycol | — | 20 | 20 | — | — | — |

TABLE 6

| No. | Comparative example 1 | 2 | 3 | 4 | 5 | 6 |
|---|---|---|---|---|---|---|
| Sol | | | | | | |
| Viscosity | 6000 | 5230 | 4900 | 53000 | 12 | 20 |
| Decision | ○ | ○ | ○ | X | ○ | ○ |

TABLE 6-continued

| No. | Comparative example | | | | | |
|---|---|---|---|---|---|---|
| | 1 | 2 | 3 | 4 | 5 | 6 |
| Rupture test | ○ | ○ | ○ | ○ | X | ○ |
| Preservation test | | | | | | |
| Before Preservation | — | 866 | 905 | 953 | 406 | 152 |
| After Preservation | — | 1360 | 1720 | 988 | 1490 | 108 |
| Decision | — | Δ | Δ | ○ | X | X |
| Water discharge phenomenon | | | | | | |
| Amount of moisture | — | 5 | 8 | 0 | 30 | 20 |
| Decision | — | Δ | Δ | ○ | X | X |
| Water absorbency | | | | | | |
| Amount of moisture | — | 70 | 79 | 46 | 0 | 0 |
| Decision | — | Δ | Δ | Δ | X | X |
| Dried product water absorbency | | | | | | |
| Decision | — | Δ | Δ | Δ | Δ | Δ |
| Gel dissolubility | | | | | | |
| Decision | — | Δ | Δ | Δ | X | X |
| Remarks | Not gelled | | | | | |

(4) Rupture Test of Gel and Evaluation

The solutions of the gel-type water absorbents (Examples 1-9 and Comparative examples 1-6) adjusted in (1) were partly poured into deep petri dishes (60 mmf×60 mm) to a slightly overflowing extent and gently left at 25° C. for 24hours to obtain gel-type water absorbents. Thereafter, the portion overflowed from the petri dish was cut flat with a knife to obtain a sample. A rupture test was evaluated using a rheometer (from ReoTec: FUDOH Rheometer D·D series). As an adapter for use in direct compression of a trial product, a 10 mm-diameter disc was attached and used to compress the trial product by 20 mm at a compression rate of 30 cm/min to observe if it is ruptured or not. The mark o is used if not ruptured and the mark × if ruptured. These measured results and evaluations are shown in Tables 5 and 6.

(5) Preservation Test of Gel and Evaluation

Two more samples of the gel-type water absorbent were prepared through the similar method as (3) and one sample was compressed under the similar condition to measure the rupture strength. The other was left at 50° C. for one week so as not to evaporate moisture, and then left at 25° C. for 24 hours to measure the rupture strength of gel under the similar condition. A variation rate of the rupture strength was evaluated as indicated with the marks o (0-150%), Δ (151-300%), and × (over 300% or below 0%) compared to the initial value before preservation. These measured results and evaluations are shown in Tables 5 and 6.

(6) Evaluation on Water Discharge Phenomenon of Gel-type Water Absorbent

A gel-type water absorbent prepared as in (3) was taken out from a petri dish into a hermetic vinyl bag that can leave as less space as possible to prevent moisture from evaporating, then left at 25° C. for one week, and subjected to visual evaluation. The moisture discharged and accumulated was sucked using a pipette. A weight ratio of the sucked moisture to gel was used to evaluate the condition as indicated with the marks o (no water discharge or below 1 weight %), Δ (water discharge of 1-below 10 weight %), and × (water discharge of 10 weight % or more relative to the gel-type water absorbent). The measured results and evaluations of the products according to the present invention and the comparative examples are shown in Tables 5 and 6.

(7) Measurement of Water Absorbency and Evaluation (Water Absorbency of Gel-type Water Absorbent)

A gel-type water absorbent prepared as in (3) was taken out from a petri dish and a 10g fragment thereof and 5 g of water were put in a 100 ml beaker. The speed of water absorbency was measured from the presence/absence of water absorbency and the amount of moisture after one hour. The absorbency was evaluated as indicated with the marks o (80-100% moisture absorbable), Δ (10-below 80% moisture absorbable), and × (below 10% moisture absorbable or not absorbable). The measured results and evaluations of the products according to the present invention and the comparative examples are shown in Tables 5 and 6.

(8) Measurement of Water Absorbency and Evaluation (Evaluation on Water Absorbency of Dried Product)

The solutions of the gel-type water absorbents adjusted in (1) were each poured into a stainless steel vat and dried in a temperature-controlled chamber at 40° C. for 24 hours to obtain a composition in the form of a sheet. This composition was observed and evaluated when water was added to restore the original weight before it was dried. As a result, they were classified into one (o) that restored to gel after it absorbed water, one (Δ) that did not restore to gel even though it partly absorbed water and one (×) that did not absorb water. The measured results and evaluations of the products according to the present invention and the comparative examples are shown in Tables 5 and 6.

(9) Measurement of Water Absorbency and Evaluation (Dissolubility of Gel-type Water Absorbent)

A gel-type water absorbent prepared as in (3) was taken out from a petri dish and a 10 g fragment thereof and 1000 g of water were put in a 2 L beaker. The speed of dissolubility was measured from the presence/absence of water absorbency and the amount of moisture after one hour. The dissolubility was evaluated as indicated with the marks o (entirely dissolved), Δ (partly undissolved), and × (not dissolved) and the presence/absence of dissolubility was confirmed. The evaluations on the products according to the present invention and the comparative examples are shown in Tables 5 and 6.

(10) Total Evaluation

Total evaluations were made with the marks: × when the items include even one ×; Δ when they include Δ; and o only when they were all o.

Other Examples with the use of the gel-type water absorbent of the present invention are described below.

Example 10

Fragrance

During agitation at 25° C. with a fan-type agitator, a tamarind seed gum was gradually added and dispersed in a polyhydric alcohol at a composition shown in Table 7. Thereafter, purified water was added and heating was started. Then, the solution was agitated for dissolution at 80° C. for 30 minutes. Other components than perfume were added and then after the temperature was adjusted down to 50° C. the perfume was added. The solution was poured into an appropriate mold and cooled to obtain a gel-type fragrance according to Example 10.

TABLE 7

| | |
|---|---|
| Purified water | 66.4 |
| Tamarind seed gum No. 1 | 2 |
| EMANON CH-60*[1] | 1 |
| Glycerin | 30 |

TABLE 7-continued

| | |
|---|---|
| Perfume | 0.5 |
| Preservative | 0.1 |
| | (%) |

*[1]Polyoxyethylene hardened castor oil (from Kao), HLB: 14

The fragrance according to Example 10 was evaluated next. With respect to the dried product water absorbency, this fragrance was left in a room at 25° C. and a humidity of 50% for 2 weeks until it reduced the weight to 50%. Then, when the weight-reduced product was allowed to absorb water by compensating for moisture so as to restore the original weight, it restored the original shape. Thereafter, when it was used as a fragrance, the fragrant odor was slightly deteriorated than before restoration though it exerted an effect sufficient to use. After two weeks, at the time of completion of the use, it was disposed in a drain hole of a sink and water was poured 3 liters per minute. After 30 minutes, it was dissolved and dissipated. It was found that this fragrance is excellent in material property and can be utilized as environmental goods. When the fragrance was tested through the evaluation methods similar to Table 5 and Table 6, it passed all the tests.

Example 11

Patch

During agitation at 25° C. with a fan-type agitator, a tamarind seed gum was gradually added and dispersed in a polyhydric alcohol at a composition shown in Table 8. Thereafter, purified water was added and heating was started. Then, the solution was agitated for dissolution at 80° C. for 30 minutes. Other components than menthol were added and dissolved, and then the menthol was added after the temperature was adjusted down to 40° C. The solution was poured into an appropriate mold and cooled to obtain a flat patch sheet according to Example 11.

TABLE 8

| | |
|---|---|
| Purified water | 66.2 |
| Tamarind seed gum No. 1 | 3 |
| EMANON CH-60 | 0.5 |
| Glycerin | 10 |
| 1,3-butyl glycol | 20 |
| Menthol | 0.1 |
| Perfume | 0.1 |
| Preservative | 0.1 |
| | (%) |

The patch according to Example 11 was evaluated next. With respect to the dried product water absorbency, this patch was adhered on a human body in a room at 25° C. and a humidity of 50% for 24 hours until it reduced the weight to 80%. Then, when the weight-reduced product was allowed to absorb water by compensating for moisture so as to restore the original weight, it restored the original shape. Thereafter, when it was similarly adhered and used for 24 hours, the refrigerant feeling of menthol was slightly deteriorated than before restoration though it had a cooling effect sufficient to use. At the time of completion of the use, it was disposed in a drain hole of a sink and water was poured 3 liters per minute. After 10 minutes, it was dissolved and dissipated. It was found that this patch is excellent in material property and can be utilized as environmental goods. When a mixture similar to this patch was subjected to the similar tests as Table 3 except for the dried product water absorbency, it passed all the tests.

Example 12

Toy for Children

During agitation at 25° C. with a fan-type agitator, a tamarind seed gum was gradually added and dispersed in a polyhydric alcohol at a composition shown in Table 9. Thereafter, purified water was added and heating was started. Then, the solution was agitated for dissolution at 80° C. for 30 minutes. Other components than a pigment were added and dissolved, and then after the temperature was adjusted down to 60° C. the pigment was added. The solution was poured into an appropriate doll mold and cooled to obtain a toy for children according to Example 12.

TABLE 9

| | |
|---|---|
| Purified water | 51.2 |
| Tamarind seed gum No. 1 | 8 |
| SUNSOFT Q-17S | 0.5 |
| Glycerin | 30 |
| Propylene glycol | 10 |
| Natural pigment | 0.1 |
| Perfume | 0.1 |
| Preservative | 0.1 |
| | (%) |

The toy for children according to Example 12 was evaluated next. With respect to the dried product water absorbency, the toy for children was left in a room at 25° C. and a humidity of 50% for one week until it reduced the weight to 60%. Then, when the weight-reduced product was allowed to absorb water by compensating for moisture so as to restore the original weight, it restored the original shape. Thereafter, when it was left for another week and two similar operations were repeated, it was restored similarly. Then, after it was floated for 12 hours on water remained in a bathroom, it was dissolved and dissipated. It was found that this toy is excellent in material property and can be utilized as enviromnental goods. When a mixture similar to this toy was subjected to the similar tests as Table 5 except for the dried product water absorbency, it passed all the tests.

Example 13

Fishing Lure

During agitation at 25° C. with a fan-type agitator, a tamarind seed gum was gradually added and dispersed in a polyhydric alcohol at a composition shown in Table 10. Thereafter, purified water was added and heating was started. Then, the solution was agitated for dissolution at 80° C. for 30 minutes. Other components than a natural pigment and an attractant were added and dissolved, and then after the temperature was adjusted down to 40° C. the natural pigment and the attractant were added. The solution was poured into an appropriate mold and cooled to obtain a worm-like molded product. Thereafter, it was dried at 40° C. for 48 hours to evaporate about 50% moisture to obtain a fishing lure according to Example 13. (The substantial content of the tamarind seed gum was 12%).

TABLE 10

| | |
|---|---|
| Purified water | 62.6 |
| Tamarind seed gum No. 1 | 6 |
| SUNSOFT Q-17S (from Taiyo Chemistries) | 0.5 |

TABLE 10-continued

| | |
|---|---|
| Glycerin | 20 |
| Propylene glycol | 10 |
| Natural pigment | 0.1 |
| Fish scale foil | 0.5 |
| Attractant | 0.1 |
| Preservative | 0.2 |
| | (%) |

The fishing lure according to Example 13 was evaluated next. This lure for fishing tackle was attached to a hook and thrown into a fish preserve in the sea that contains no fish. It was pulled up after one hour and the weight was measured double the original weight because of water absorption but completely dissolved after 3 hours. It was found that this lure is excellent in material property and can be utilized as environmental goods. Thereafter, the lure was thrown three times into a fish preserve that contains fish, and was bitten by fish within 3 minutes. When the same amount of the attractant is mixed into a lactate polymer, 10 minutes or longer were required three times until fish bit the lure. Therefore, the appropriate dissolubility dissolves out the attractant and facilitates attraction of fish as the merit.

The invention claimed is:

1. A water absorbent gel, comprising 5-50% by weight of a tamarind seed polysaccharide including 90% or more dietary fiber, 1% or less protein and 1% or less ash; and 20-35% by weight of a polyhydric alcohol with 2-5 valences, selected from the group consisting of glycerin, 1,3-butylene glycol, propylene glycol, dipropylene glycol, hexylene glycol, 1,2-pentane diol, 1,2 hexane diol, erythritol, diglycerin, and peneterythritol.

2. The water absorbent gel according to claim 1, comprising a tamarind seed polysaccharide comprising 92% or more dietary fiber, 0.5% or less protein and 0.5% or less ash, and water-soluble organic substance.

3. The water absorbent gel according to claim 1, further comprising a volatile active ingredient.

4. The water absorbent gel according to claim 1, wherein said water-soluble organic substance further comprises a water-soluble surfactant with an HLB value of 10-20.

5. A fragrance, comprising said water absorbent gel according to claim 1 as a base material.

6. A water absorbent gel comprising 5-50% by weight of a tamarind seed polysaccharide including 90% or more dietary fiber, 1% or less protein and 1% or less ash; and 20-35% by weight of a polyhydric alcohol with 2-5 valences, selected from the group consisting of glycerin, 1,3-butylene glycol, and propylene glycol.

* * * * *